(12) United States Patent
Beyaert et al.

(10) Patent No.: US 7,893,026 B2
(45) Date of Patent: Feb. 22, 2011

(54) TREATMENT OF EGFR-DEPENDENT TUMORS BY ABIN (A20 -BINDING INHIBITOR OF NF KAPPAB)

(75) Inventors: Rudi Beyaert, Zingem (BE); Hilde Revets, Meise (BE); Lieven Huang, Ledeberg (BE)

(73) Assignees: VIB VZW, Zwijnaarde (BE); Universiteit Gent, Ghent (BE); Vrije Universiteit Brussel, Brussels (BE)

( * ) Notice: Subject to any disclaimer, the term of this patent is extended or adjusted under 35 U.S.C. 154(b) by 203 days.

(21) Appl. No.: 11/918,559

(22) PCT Filed: Apr. 11, 2006

(86) PCT No.: PCT/EP2006/061528
§ 371 (c)(1),
(2), (4) Date: Jun. 23, 2008

(87) PCT Pub. No.: WO2006/108844
PCT Pub. Date: Oct. 19, 2006

(65) Prior Publication Data
US 2009/0023650 A1    Jan. 22, 2009

(30) Foreign Application Priority Data
Apr. 14, 2005    (EP)    ................... 05102967

(51) Int. Cl.
*A61K 38/00*    (2006.01)
(52) U.S. Cl. .......................................... 514/12; 514/21
(58) Field of Classification Search ........................ None
See application file for complete search history.

(56) References Cited

U.S. PATENT DOCUMENTS

| 6,673,897 B1 | 1/2004 | Beyaert et al. |
| 7,094,756 B2 | 8/2006 | Beyaert et al. |
| 7,615,617 B2 * | 11/2009 | Robinson et al. ............ 530/412 |

FOREIGN PATENT DOCUMENTS

| WO | WO 99/57133 | 11/1999 |
| WO | WO 03/000280 A2 | 1/2003 |

OTHER PUBLICATIONS

Ibragimova and Eade (Biophysical Journal, Oct. 1999, vol. 77, pp. 2191-2198).*
Zhang et al (Biochem Biophys Res Comm, 2002, vol. 297, pp. 17-23).*
ATCC Website (information for Saosi-2 cells, downloaded from the Web, Oct. 25, 2009).*
Abstract of Su (Zhonghua Bing Li Xue Za Zhi, 1995, vol. 24, pp. 93-95).*
Heyninck et al., Structure-function analysis of the A20-binding inhibitor of NF-kappaB activiation, ABIN-1, FEBS Letters, Feb. 11, 2003, pp. 135-140, vol. 536, No. 1-3, Elsevier, Amsterdam, NL.
Van Huffel et al., Identification of a novel A20-binding inhibitor of nuclear factor-kappa B activation termed ABIN-2, Journal of Biological Chemistry, Aug. 10, 2001, pp. 30216-30223, vol. 276, No. 32.
PCT International Search Report, PCT/EP2006/061528, dated Jul. 18, 2006.

* cited by examiner

*Primary Examiner*—Karen A Canella
(74) *Attorney, Agent, or Firm*—TraskBritt, P.C.

(57) ABSTRACT

The present invention relates to the treatment of epidermal growth factor-family receptor- (ErbB-) dependent tumors. More specifically, the present invention relates to the use of ABIN for the preparation of a medicament to inhibit epidermal growth factor- (EGF-) induced proliferation, and to treat ErbB-dependent tumors.

3 Claims, 4 Drawing Sheets

SEQUENCE LISTING

```
<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: forward primer in example 4

<400> SEQUENCE: 1
cgggatccgc catgggtgcg ccggtgcc                                              28

<210> SEQ ID NO 2
<211> LENGTH: 28
<212> TYPE: DNA
<213> ORGANISM: Artificial Sequence
<220> FEATURE:
<223> OTHER INFORMATION: reverse primer in example 4

<400> SEQUENCE: 2
ccccaagctt aaatgaccca ctgcagcc                                              28
```

US 7,893,026 B2

TREATMENT OF EGFR-DEPENDENT TUMORS BY ABIN (A20-BINDING INHIBITOR OF NF KAPPAB)

CROSS-REFERENCE TO RELATED APPLICATIONS

This is a national phase entry under 35 U.S.C. §371 of International Patent Application Serial No. PCT/EP2006/061528, filed Apr. 11, 2006, and published in English as International Patent Publication WO 2006/108844 A1 on Oct. 19, 2006, which application claims priority to European Patent Application Serial No. 05102967.6 filed Apr. 14, 2005.

TECHNICAL FIELD

The present invention relates to the treatment of epidermal growth factor-family receptor- (ErbB-) dependent tumors. More specifically, the present invention relates to the use of ABIN for the preparation of a medicament to inhibit epidermal growth factor- (EGF-) induced proliferation, and to treat ErbB-dependent tumors.

BACKGROUND

Epithelial growth factor receptor (EGFR) is a transmembrane protein that is implicated in the progression of many epithelial cancer types. Indeed, several human cancers including, but not limited to, non-small cell lung cancer, squamous cell carcinoma of head and neck cancer, esophageal and gastric cancer, colon cancer, pancreatic cancer, breast cancer, ovarian cancer, bladder cancer, vulvar squamous carcinoma, human androgen-insensitive prostate cancer, renal carcinoma, glioma and glioblastoma displaying EGFR RNA and/or protein overexpression.

EGFR is one of the four homologous transmembrane ErbB proteins that mediate actions of a family of growth factors including EGF, transforming growth factor-α, and the neuregulins. More specifically, EGFR regulates the intracellular effects of ligands such as EGF and TGF-α. Binding of ligands to the EGFR extracellular domains (collectively called the ectodomain) results in allosteric transitions leading to receptor dimerization, protein kinase activation, trans-autophosphorylation, and initiation of signaling cascades (Yarden et al., 2001). The EGFR also interacts with its three known homologues, ErbB2 (HER2), ErbB3 (HER3) and ErbB4 (HER4) in a ligand-dependent fashion to form heterodimers. Heterodimerization of two different members of the ErbB family increases the diversity of ligands recognized by individual receptors and results in an expansion in the repertoire of signaling pathways that can be activated by a given receptor (Jorissen et al., 2003; Olayloye et al., 2000).

Activation of the EGFR induces several transduction pathways inside the cell and contributes to many cellular processes such as cell proliferation, inhibition of apoptosis and angiogenesis. Apoptosis and its underlying pro-apoptotic signaling pathways are often decreased in cancer cells (Zhivotovsky and Orrenius, 2003). Interaction of EGF with its receptor EGFR activates cell proliferation and also blocks death signals (Navolanic et al., 2003). At least in some cases, NF-κB-dependent up-regulation of proliferative and anti-apoptotic genes is responsible for increased cell survival and tumorigenesis (Aggarwal, 2004). In unstimulated cells, NF-κB is usually kept inactive in the cytoplasm through association with inhibitory proteins of the IκB (Inhibitor of NF-κB) family. In response to several stimuli, including pro-inflammatory cytokines such as tumor necrosis factor (TNF) and interleukin-1 (IL-1), IκBα is phosphorylated at serines 32 and 36 by the activity of the IκB kinase (IKK) complex, ubiquitinated and degraded by the proteasome. This allows NF-κB to enter the nucleus, where it is further regulated by phosphorylation, acetylation and interactions with co-activators and co-repressors to transcribe both anti-apoptotic and proliferative genes. It has previously been reported that EGF also induces NF-κB nuclear levels in cell types such as A431 cells and in several breast cancer cell lines that overexpress EGF receptors (Biswas et al., 2003). However, the regulation of NF-κB activity by growth factors such as EGF is less well understood compared to the well-known NF-κB pathway that is activated by TNF. In carcinoma cells that overexpress EGF receptor family members, EGF has been shown to induce IκBα degradation and NF-κB DNA binding (Sun and Carpenter, 1998; Biswas et al., 2000). Likewise, it has been shown that heregulin induces an IKK-dependent, NF-κB-mediated proliferation of estrogen receptor negative, ErbB2 overexpressing breast cancer cells (Biswas et al., 2004) and potentiates ErbB3-mediated NF-κB activation (Bhat-Nakshatri et al., 2002). In addition, up-regulation of IKKα and IKKβ by the integrin-linked kinase/Akt pathway is required for the ErbB2-mediated NF-κB anti-apoptotic pathway (Makino et al., 2004). Additionally, NF-κB-inducing kinase (NIK) has been reported to be complexed with the EGF receptor, which potentiates EGF activation of NF-κB (Chen et al., 2003). Moreover, NIK was shown to potentiate ErbB2/ErbB4-induced NF-κB activation (Chen et al., 2003).

Consistent with EGF-controlled activation of NF-κB, two recent reports have shown positive regulation of the c-fos gene by EGF in quiescent fibroblasts (Anest et al., 2004) and the EAAT2 glutamate transporter gene in astroglioma cells (Sitcheran et al., 2005), through a mechanism involving constitutive nuclear localization of NF-κB. In the latter two cases, EGF-induced NF-κB activation was independent of signaling to IκB. Clearly, further studies are necessary to understand the regulation of EGF-responsive genes by NF-κB.

Due to its role in tumor growth and proliferation, EGFR has been a preferred target for the development of anti-cancer drugs. A first class of anti-EGFR drugs consists of preferably humanized monoclonal antibodies against the extracellular domain of the receptor. Such antibodies have, amongst others, been disclosed in WO 89/06692 and in U.S. Pat. No. 5,470,571. A second class of inhibitors are small molecules that compete with ATP for binding to the ATP site in the EGFR tyrosine kinase domain and, therefore, block the signaling cascade. Gefitinib (ZD1839, Iressa®) is an example of this class. Although these compounds are available, there is still a need for other products that can block EGFR-dependent tumor formation.

Surprisingly, we found that ABIN is also capable of blocking EGF-EGFR-induced cell proliferation. ABIN-1, ABIN-2, and ABIN-3 are three proteins that have been described as inhibitors of TNF, IL-1 and LPS-mediated activation of NF-κB (Heyninck et al., 1999; Van Huffel et al., 2001; Genbank AJ320534). In addition, NF-κB activation mediated by overexpression of the signaling proteins TRADD, RIP, TRAF2 or TRAF6 can be attenuated by co-expression of the ABINs. However, the ABINs have no effect on NF-κB activation induced by overexpression of NIK, IKKβ or the p65 NF-κB subunit. These results indicate that the ABINs act upstream of the IKK complex. Since signaling upstream of IKK is receptor- and stimulus-dependent, the inhibitory effect of ABINs is most likely not applicable to all cases of NF-κB activation, but limited to well-defined pathways. Up to now, there was no indication that ABIN could block ErbB and, more specifically, the EGFR-dependent NF-κB activation, and subsequent EGF-EGFR-dependent proliferation.

A first aspect of the invention is the use of ABIN or an ABIN derivative, or a functional fragment thereof, for the preparation of a medicament to treat an ErbB overexpressing tumor. An ErbB overexpressing tumor means that the tumor tissue shows a higher expressing level of the ErbB member than the same healthy tissue. Preferably, the ErbB overexpressing tumor is selected from the group consisting of EGFR overexpressing tumors and ErbB2 overexpressing tumors. Even more preferably, the ErbB overexpressing tumor is an EGFR overexpressing tumor. The ABIN protein family is known to the person skilled in the art and includes ABIN-1, ABIN-2 and ABIN-3. ABIN and ABIN derivatives as used herein include both nucleic acid, encoding ABIN protein, and the protein itself. Derivatives, as used herein include biologically active mutants and variants of ABIN, and fusion proteins comprising ABIN or a biological active mutant or variant. One preferred embodiment of a derivative is a fusion protein of ABIN with a peptide that promotes delivery of the fusion protein into the cell, such as TAT-derived peptides. Another preferred embodiment of a derivative is a fusion protein of ABIN with a nanobody that can direct the fusion protein to tumor cells. A functional fragment of ABIN or an ABIN derivative is a fragment comprising at least the minimal active domain (MAD). Preferably, the functional fragment consists of the MAD. The MAD as used herein is the minimal domain that still exerts its inhibition on TNF-induced NF-κB activation (Heyninck et al., 2003). The MAD of human ABIN-1 consists of aa 431-588 of human ABIN-1 (accession number AAG42154). On the base of sequence comparison, the MAD of ABIN 2 may be defined as aa 274-429 of ABIN-2 (accession number CAC34835) and the MAD of human ABIN-3 as aa 174-325 of ABIN-3 (accession number AAL02151). The MAD of mouse ABIN-1 consists of aa 444-601 of mouse ABIN-1 (accession number CAB44240) and the MAD of mouse ABIN-2 consists of aa 286-430 of mouse ABIN-2 (accession number CAC34841). Preferably, the functional fragment comprises the MAD of human ABIN-1, more preferably, the functional fragment consists of the MAD of human ABIN-1. The functional fragments may be used on its own, or in a fusion protein as described above.

Nucleic acids encoding ABIN or ABIN derivatives, or functional fragments thereof, can be used in gene therapy. Suitable vectors are known to the person skilled in the art. ABIN and ABIN-derived proteins may be used for direct delivery into the tumor cells. Methods for delivery to tumor cells are known to the person skilled in the art and include, but are not limited to, coupling the protein to tumor-specific antibodies or the use of tumor-specific immunoliposomes. ErbB overexpressing tumors, especially EGFR overexpressing, ErbB2 overexpressing and ErbB3 overexpressing tumors, are known to the person skilled in the art and include, but are not limited to, non-small cell lung cancer, squamous cell carcinoma of head and neck cancer, esophageal and gastric cancer, colon cancer, pancreatic cancer, breast cancer, ovarian cancer, bladder cancer, vulvar squamous carcinoma, human androgen-insensitive prostate cancer, renal carcinoma, glioma and glioblastoma. Preferably, the ErbB overexpressing tumor is squamous carcinoma or human androgen-insensitive prostate cancer.

Another aspect of the invention is the use of ABIN or an ABIN derivative, or a functional fragment thereof, to block EGF-EGFR-dependent cell proliferation.

Still another aspect of the invention is the use of ABIN or an ABIN derivative, or a functional fragment thereof, to inhibit ErbB-dependent NF-κB activation. Preferably, ErbB-dependent NF-κB activation is EGRF-dependent NF-κB activation.

DETAILED DESCRIPTION OF THE INVENTION

EXAMPLES

Example 1

EGF Signaling Activates NF-κB

Figure 1:
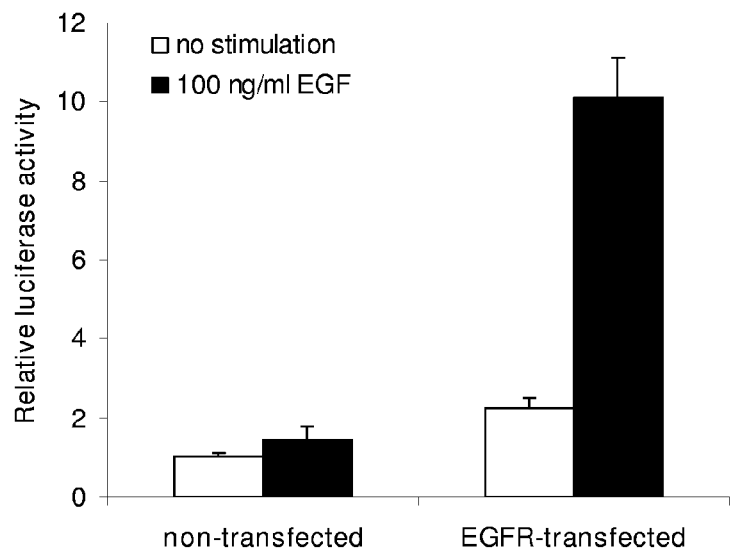
FIG. 1: EGF activation of NF-κB in EGFR-transfected HEK293T cells. HEK293T cells were transiently transfected with pNFconluc and pUT651, either together or separate, with an EGFR-encoding expression vector. After 24 hours, cells were left untreated (grey bars) or stimulated for six hours with EGF (black bars). NF-κB activity was determined via luciferase and β-galactosidase reporter gene tests and is shown as relative luciferase activity.

Embryonic kidney epithelial HEK293T cells were grown in 24-well plates (50,000 cells/well) in DMEM supplemented with 10% fetal calf serum, 2 mM L-Glutamine, 0.4 mM sodium pyruvate and antibiotics, and transiently transfected by DNA calcium phosphate coprecipitation with the following plasmids: an EGFR-encoding plasmid (pMT2-EGFR obtained from Dr. Roovers (University of Utrecht), transfected at 200 ng/μg total DNA), pNFconluc (100 ng/μg), encoding the luciferase reporter gene driven by a minimal NF-κB-responsive promoter (Kimura et al., 1986), and pUT651 (100 ng/μg) encoding β-galactosidase driven by the constitutively active CMV promoter (Eurogentec, Seraing, Belgium). The day after transfection, cells were either non-stimulated or stimulated for 24 hours with 100 ng/ml EGF. Cells were subsequently lysed in lysis buffer (25 mM Tris-phosphate pH 7.8, 2 mM dithiothreitol, 2 mM 1,2-cyclohex-aminediaminetetraacetic acid, 10% glycerol and 1% Triton X-100). Inducible promoter activity was measured by measuring the luciferase and β-galactosidase activity present in cell extracts. Luciferase values were normalized for β-galactosidase values in order to correct differences in transfection efficiency. As shown in FIG. 1, EGF addition to EGFR-transfected HEK293T cells induced NF-κB activation.

Figure 2:
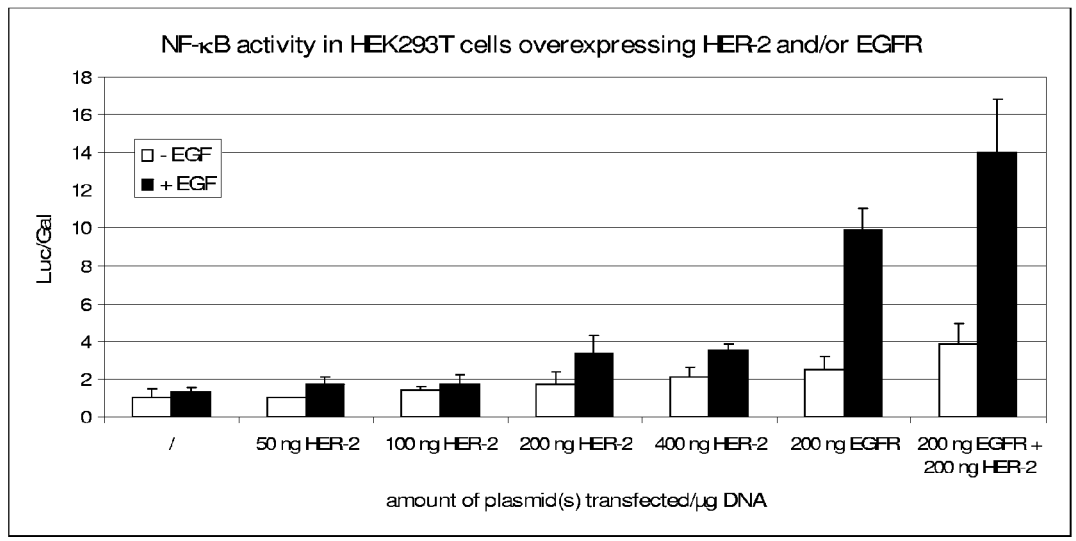
FIG. 2: NF-κB reporter gene assay in HEK293T cells transfected with various amounts of HER-2 expression plasmid: 50,000 HEK293T cells/well were seeded in 24-well plates in complete medium. On the next day, cells were transfected with 0, 50, 100, 200 or 400 ng/μg total DNA of the HER-2 expression plasmid (pCDNA3.1). As a control, cells were also transfected with the EGFR expression plasmid. In addition, 200 ng/μg of both plasmids were cotransfected. After six hours, transfection medium was replaced with complete medium. The following day, cells were serum starved in serum-free medium supplemented with ITS. Twenty-four hours later, part of the cells were stimulated with 100 ng/ml EGF for six hours. Cells were finally lysed in 200 μl 1× luciferase lysis buffer.

In a similar way, the effect of HER-2 expression on NF-κB activation was measured. HEK293T cells were transfected with increasing amounts of HER2 DNA. As can be seen in FIG. 2, the presence of HER2 is sufficient to obtain EGF-induced NF-κB activation, but the signal is strongly increased when both EGFR, as well as HER2, are present.

Example 2

Figure 3:
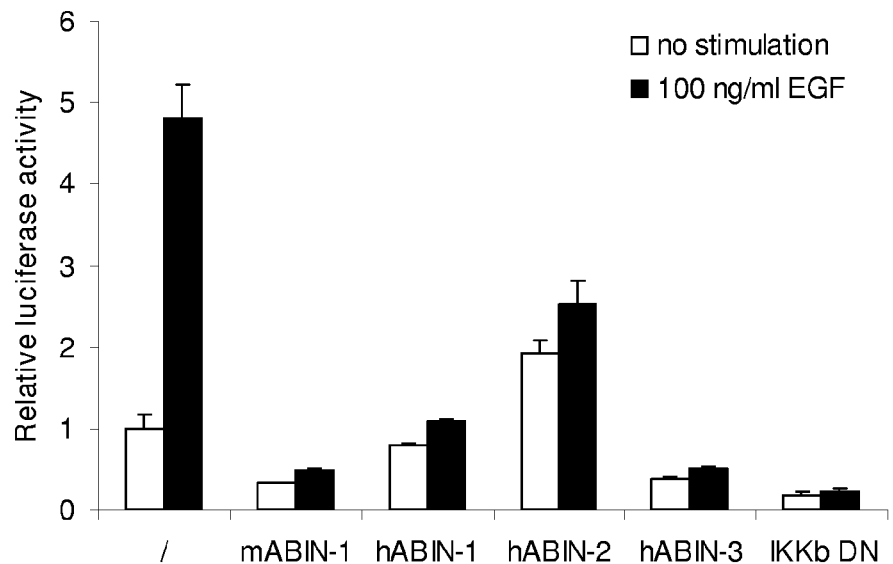
FIG. 3: Effect of different ABINs on EGF-induced NF-κB activation. HEK293T cells were transiently transfected with expression vectors encoding the different ABINs or an IKKβ kinase-defective dominant-negative mutant (IKKβ-DN), together with an EGFR-encoding plasmid, pNFconluc and pUT651. After transfection, cells were serum starved left untreated (grey bars) or stimulated for six hours with EGF (black bars). NF-κB activity was determined via luciferase and β-galactosidase reporter gene tests and is shown as relative luciferase activity.
Figure 4:
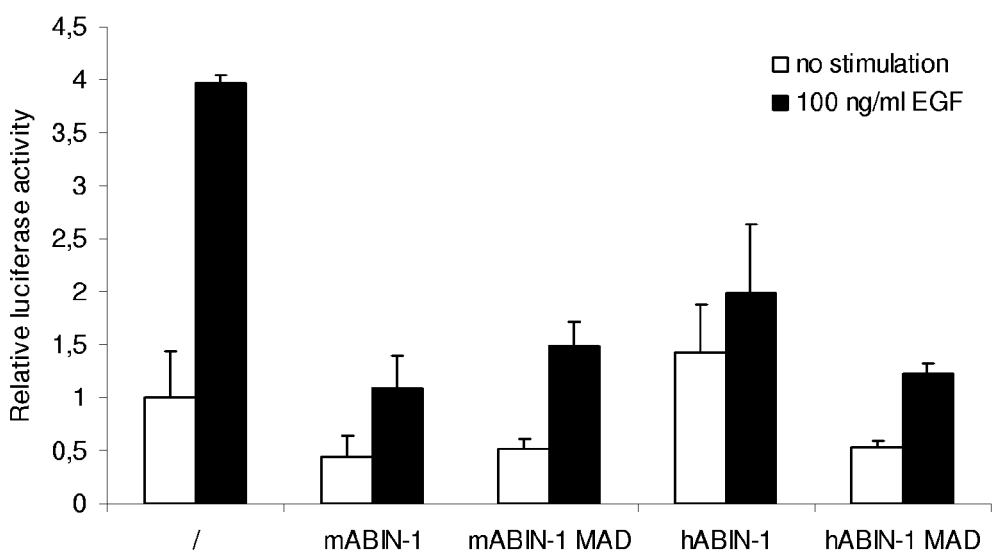
FIG. 4: Effect of the minimal active domains (MAD) of mABIN-1 and hABIN-1 on EGF-induced NF-κB activation. HEK293T cells were transiently transfected with expression vectors encoding the different ABIN molecules, together with an EGFR-encoding plasmid, pNFconluc and pUT651. After transfection, cells were serum starved for 24 hours in ITS (insulin/transferin/selenium) containing serum-free medium. Cells were then left untreated (grey bars) or stimulated for six hours with EGF (black bars). NF-κB activity was determined via luciferase and ε-galactosidase reporter gene tests and is shown as relative luciferase activity.

Full-length ABINs, as Well as their Minimal Active Domain (Mad), Inhibit EGF-mediated NF-κB Activation To analyze the NF-κB-inhibiting effects of ABINs and their minimal active domain (MAD), EGFR-expressing HEK293T cells were transiently transfected in 24-well plates (50,000 cells/well) with expression plasmids encoding murine ABIN-1 (100 ng/μg), mABIN1-MAD (aa 444-601) (100 ng/μg), human ABIN-1 (100 ng/μg), hABIN-1-MAD (100 ng/μg), hABIN-2 (100 ng/μg) or hABIN-3 (100 ng/μg). After transfection, cell were serum-starved for 24 hours in serum-free medium supplemented with ITS (Insulin-Transferrin-Selenium supplement obtained from Invitrogen), after which they were either non-stimulated or stimulated for six hours with 100 ng/ml EGF. The effect of ABIN on EGF-induced activation of NF-κB was studied by luciferase reporter tests. As shown in FIG. 3, all full-length ABINs inhibit EGF-mediated NF-κB activation. A dominant-negative kinase-defective mutant of IKKβ, IKKb-DN, thereby strongly repressing NF-κB activation, was used as a positive control (100 ng/μg). Overexpression of the minimal active domains of mABIN-1 (50 ng/μg) and hABIN-1 (100 ng/μg) resulted in a similar inhibition of EGF-mediated NF-κB activation as that provided by their full-length counterparts (FIG. 4).

Figure 5:
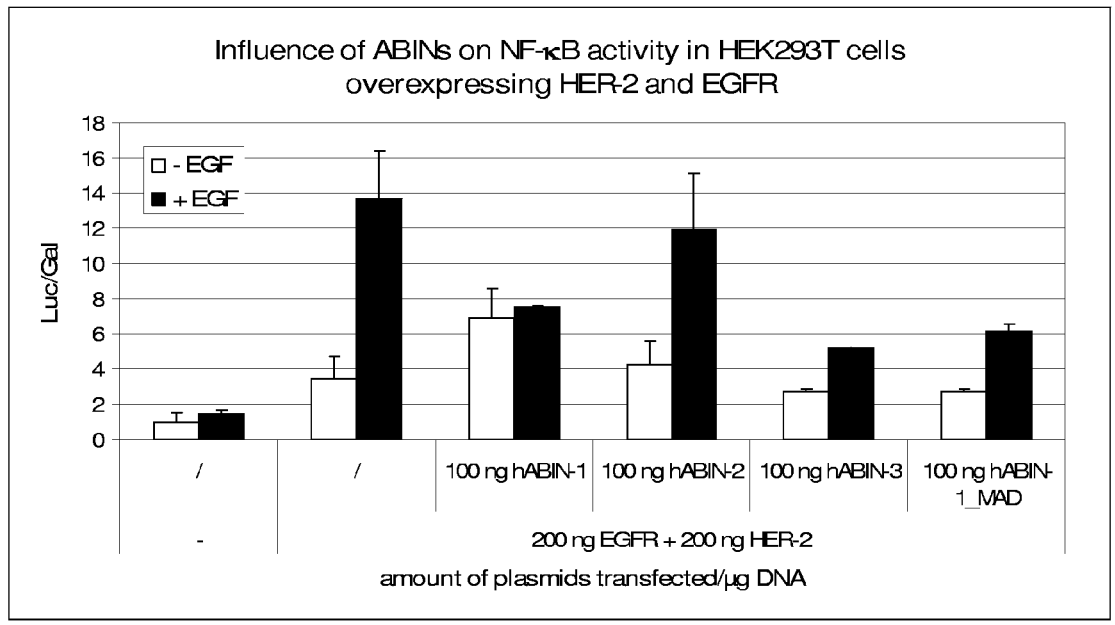
FIG. 5: Effect of ABINs on NF-κB activity in HEK293T cells transfected with both HER-2 and EGFR expression plasmids. Experiment was performed as described in FIG. 2. Cells were transfected with 200 ng of both expression plasmids. hABIN-1, hABIN-2, hABIN-3 and hABIN-1_MAD were all transfected at 100 ng/μg DNA.

In a similar way, the different ABINs, as well as their minimal active domain, strongly repressed the EGF-induced activation of NF-κB when both EGFR and HER-2 were present as receptors (FIG. 5).

Example 3

Figure 6:
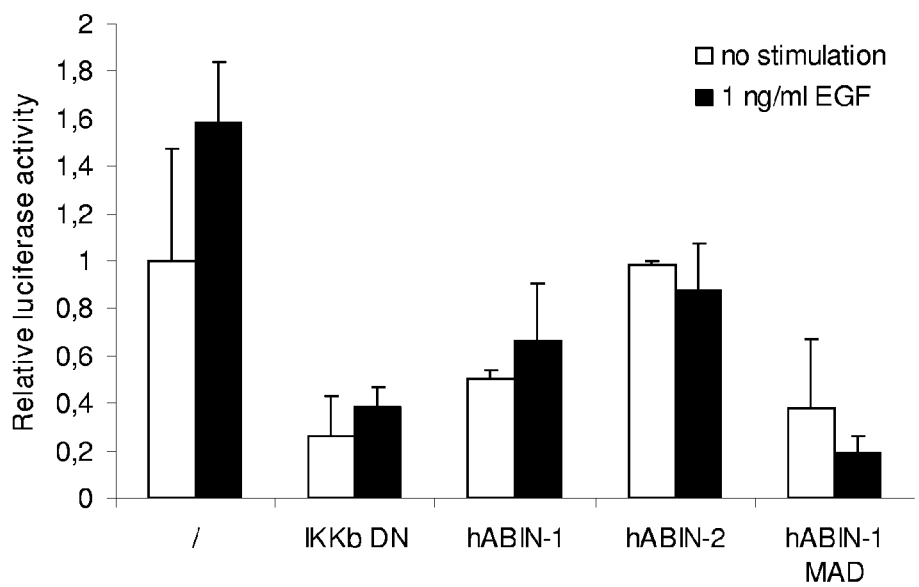
FIG. 6: Effect of ABINs and MAD domains on EGF-induced NF-κB activation in A431 cancer cells. A431 cells were transiently transfected with expression vectors encoding the different ABINs or IKKβ-DN together with pNFconluc and pUT651. After 48 hours, cells were serum-starved overnight and then left untreated or stimulated with 1 ng/ml EGF for six hours. NF-κB activity was determined via luciferase and β-galactosidase reporter gene tests and is shown as relative luciferase activity.

ABINs and their MADs Inhibit EGF-mediated NF-κB Activation in A431 Human Carcinoma Cells A431 carcinoma cells were grown in DMEM supplemented with 10% fetal calf serum, 2 mM L-Glutamine, 0.4 mM sodium pyruvate, 1 mM non-essential amino acids, 100 IU/ml penicillin and 0.1 mg/ml streptomycin. To determine whether or not ABINs and their MAD domains can block NF-κB activity following EGF treatment of human epidermoid carcinoma A431 cells, which overexpress EGF receptors ($2 \times 10^6$ receptors per cell), A431 cells were seeded in six-well plates (150,000 cells/well). The following day, cells were transiently transfected with expression vectors encoding the different ABIN constructs (2 μg/well) and their effect on EGF-induced NF-κB activation was studied by luciferase reporter assays (both pNFconluc and pUT651 were applied at 2 μg/well). Forty-eight hours after transfection, cells were serum starved overnight (serum-free medium supplemented in ITS). Cells were then either stimulated with 1 ng/ml EGF for six hours or left untreated. Overexpression of both hABIN-1 and hABIN-2 clearly inhibited EGF-mediated NF-κB activation in A431 cells (FIG. 6). hABIN1-MAD was even more potent in inhibiting NF-κB activity in A431 cells upon EGF stimulation, as compared to full-length hABIN-1. As expected, IKKb DN strongly inhibited NF-κB activity.

Example 4

Adenoviral Expression of ABIN Inhibits the Proliferative Capacity of A431 Human Vulvar Squamous Carcinoma and Human Androgen-insensitive DU145 Prostate Cancer Cells Recombinant adenoviruses for mABIN-1 were prepared as described previously (El Bakkouri et al., 2005). Briefly, the murine ABIN-1 cDNA, N-terminally fused to an E-tag, was amplified via PCR with a forward 5'-cgggatccgccatgggtgcgc-cggtgcc-3' primer and reverse 5'-ccccaagcttaaatgacccactg-cagcc-3' primer. A recombinant adenoviral vector AdABIN-1 was generated by cloning the ABIN-1 PCR fragment into a BamHI and HindIII opened pACpLpA.CMV shuttle vector (Gomez-Foix et al., 1992) and co-transfected with the rescue plasmid pJM17 (McGrory et al., 1988) (which encodes the adenovirus dl309 genome, lacking E1 and E3 functions) into HEK293 cells via calcium phosphate coprecipitation. Recombinant plaques were isolated, extracted DNA was verified via PCR, and expression of the correct transgene from the ubiquitously active cytomegalovirus (CMV) promoter was confirmed by means of Western blotting. Recombinant adenoviruses for the other ABINs were prepared in a similar way. Control viruses without transgene (AdRR5) or expressing the β-galactosidase gene (AdLacZ), and a virus expressing the IκBα super-repressor (AdIκBα$^s$) were generated with the same pJM17 adenoviral backbone vector. The IκBα super-repressor means a nondegradable mutant form of IκB-α with S32A and S36A mutations (Grempler et al., 2004). The latter locks NF-κB in a cytosolic protein complex, preventing its nuclear action. High titer virus stocks were prepared in HEK293 cells and purified via single CsCl banding. Titers were determined via plaque assay in HEK293 cells and calculated as plaque-forming units (pfu) per ml virus stock.

A431 and DU145 cells were maintained in DMEM supplemented with 10% fetal calf serum, 2 mM L-Glutamine, 0.4 mM sodium pyruvate, 1 mM nonessential amino acids, 100 IU/ml penicillin and 0.1 mg/ml streptomycin.

Figure 7:
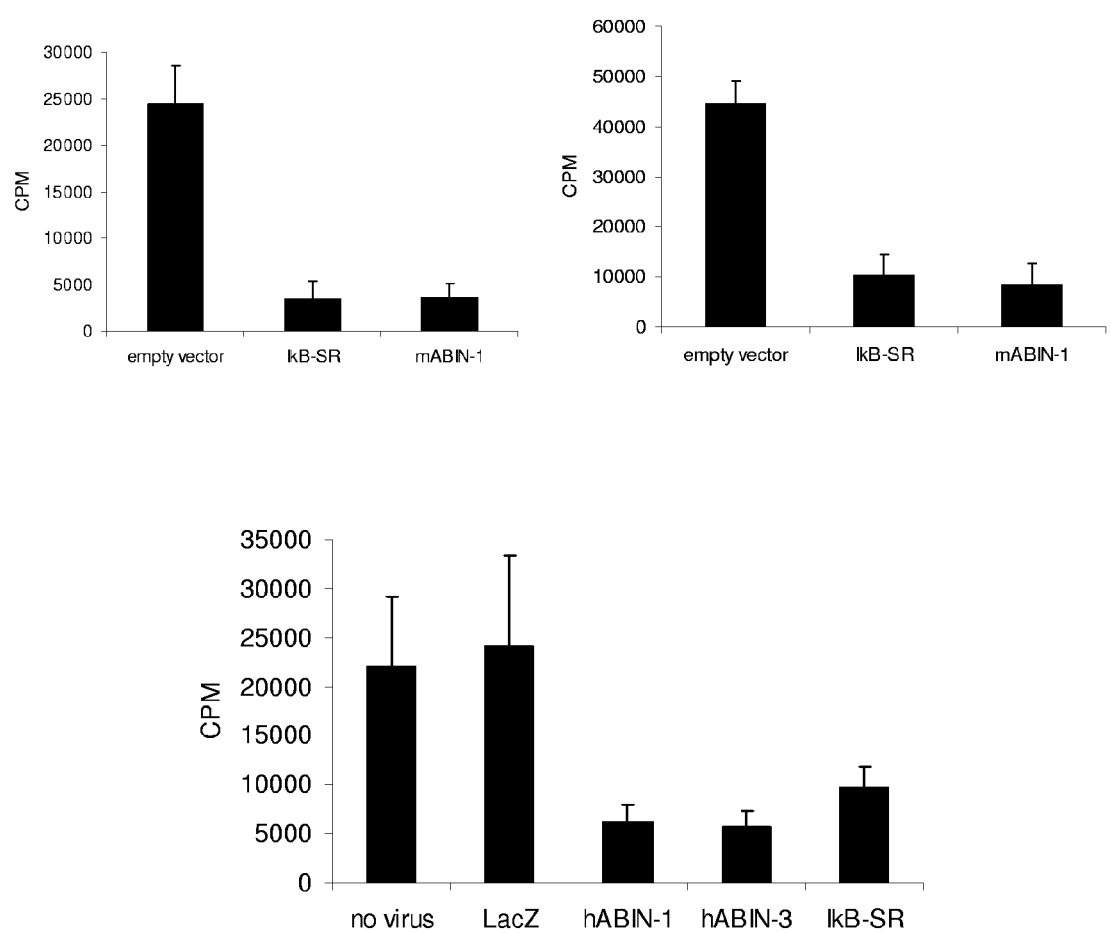
FIG. 7: A431 (upper left panel and lower panel) and DU145 (upper right panel) cells were seeded in six-well plates (150,000 cells/well) and adenovirally transfected with 200 MOI of a recombinant adenovirus expressing either no transgene (RR5), the IβBα super-repressor mutant (IκB-SR), mABIN-1, hABIN-1, hABIN-3, or LacZ, as indicated. Four hours after transfection, cells were reseeded into 96-well plates (2000 cells/well) in complete medium. Twenty-four hours after transfection, cells were pulsed with 0.5 μCi $^3$H-thymidine (per well) and grown for 72 hours, after which the cells were frozen. Cells were subsequently thawed and manually embedded on glass fiber membranes. After washing, the filter membranes are air-dried and counted using a β-counter. Lower panel was obtained by transfecting A431 cells seeded in 96-well plates (2000 cells/well) with 200 MOI of recombinant adenovirus. Cells were further treated as described above.

DU145 cells ($2\times10^5$ EGF receptors per cell; MacDonald et al., 1990) and A431 cells ($2\times10^6$ EGF receptors per cell; Haigler et al., 1978) were adenovirally transfected with 200 MOI of mABIN-1, hABIN-1, hABIN-3, the IκBα super-repressor (IκB-SR), LacZ, or the empty vector RR5, and their effects on the proliferation of the cancer cells was monitored via incorporation of $^3$H-thymidine. As shown in FIG. 7, ABINs inhibited the proliferation of both cancer cell lines to the same extent as the IκBα super-repressor did.

REFERENCES

Aggarwal B. B. (2004). Nuclear factor-kappaB: the enemy within. *Cancer Cell* 6:203-208.

Anest V., P. C. Cogswell, and A. S. Baldwin Jr. (2004). IkappaB kinase alpha and p65/RelA contribute to optimal epidermal growth factor-induced c-fos gene expression independent of IkappaBalpha degradation. *J. Biol. Chem.* 279:31183-9.

Bhat-Nakshatri P., C. J. Sweeney, and H. Nakshatri (2002). Identification of signal transduction pathways involved in constitutive NF-κB activation in breast cancer cells. *Oncogene* 21:2066-2078.

Biswas D. K., A. P. Cruz, E. Gansberger, and A. B. Pardee (2000). Epidermal growth factor-induced nuclear factor kappa B activation: A major pathway of cell-cycle progression in estrogen-receptor negative breast cancer cells. *Proc. Natl. Acad. Sci. U.S.A.* 97:8542-7.

Biswas D. K., K. J. Martin, C. McAllister, A. P. Cruz, E. Graner, S. C. Dai, and A. B. Pardee (2003). Apoptosis caused by chemotherapeutic inhibition of nuclear factor-kappa B activation. *Cancer Res.* 63:290-295.

Biswas D. K., Q. Shi, S. Baily, I. Strickland, S. Ghosh, A. B. Pardee, and J. D. Iglehart (2004). NF-kappa B activation in human breast cancer specimens and its role in cell proliferation and apoptosis. *Proc. Natl. Acad. Sci.* 101:10137-10142.

Chen D., L. G. Xu, L. Chen, L. Li, Z. Zhai, and H. B. Shu (2003). NIK is a component of the EGF/heregulin receptor signaling complexes. *Oncogene* 22:4348-55.

El Bakkouri K., A. Wullaert, M. Haegman, K. Heyninck, and R. Beyaert (2005). Adenoviral gene transfer of the NF-κB inhibitory protein ABIN-1 decreases allergic airway inflammation in a murine asthma model. *J. Biol. Chem.* (in press).

Gomez-Foix A., W. Coats, S. Baque, T. Alam, R. Gerard, and C. Newgard (1992). Adenovirus-mediated transfer of the muscle glycogen phosphorylase gene into hepatocytes confers altered regulation of glycogen metabolism. *J. Biol. Chem.* 267:25129-25134.

Grempler R., A. Kienitz, T. Werner, M. Meyer, A. Barthel, F. Ailett, C. Sutherland, R. Walther, and D. Schmoll (2004). Tumor necrosis factor alpha decreases glucose-6-phosphatase gene expression by activation of nuclear factor kappaB. *Biochem. J.* 382:471-479.

Haigler H., J. F. Ash, S. J. Singer, and S. Cohen (1978). Visualization by fluorescence of the binding and internalization of epidermal growth factor in human carcinoma cells A-431. *Proc. Nat. Acad. Sci. USA* 75:3317-3321.

Heyninck K., D. De Valck, W. Vanden Berghe, W. Van Crieckinge, R. Contreras, W. Fiers, G. Haegeman, and R. Beyaert (1999). The zinc finger protein A20 inhibits TNF-induced NF-κB-dependent gene expression by interfering with a RIP- or TRAF2-mediated transactivation signal and directly binds to a novel NF-κB-inhibiting protein ABIN. *J. Cell Biol.* 145:1471-1482.

Heyninck K., M. M. Kreike, and R. Beyaert (2003). Structure-function analysis of the A20-binding inhibitor of NF-κB activation, ABIN-1. *FEBS LETT.* 536:135-140.

Jorissen R. N., F. W. Walker, N. Pouliot, T. P. J. Garrett, C. W. Ward, and A. W. Burgess (2003). Epidermal growth factor receptor: mechanisms of activation and signaling. *Exp. Cell Res.* 284:31-53.

Kimura A., A. Israel, O. Le Bail, and P. Kourilsky (1986). Detailed analysis of the mouse H-2 Kb promoter: enhancer-like sequences and their role in the regulation of class I gene expression. *Cell* 44:261-72.

MacDonald A., G. D. Chisholm, and F. K. Habib (1990). Production and response of a human prostatic cancer line to transforming growth factor-like molecules. *Br. J. Cancer* 62:579-584.

Makino K., C. P. Day, S. C. Wang, Y. M. Li, and M. C. Hung (2004). Up-regulation of IKKalpha/IKKbeta by integrin-linked kinase is required for Her2/neu-induced NF-kappaB antiapoptotic pathway. *Oncogene* 23:3883-3887.

McGrory W., D. Bautista, and F. Graham (1988). A simple technique for the rescue of early region I mutations into infectious human adenovirus type 5. *Virology* 163:614-617.

Navolanic P. M., L. S. Steelman, and J. A. McCubrey (2003). EGFR family signaling and its association with breast cancer development and resistance to chemotherapy. *Int. J. Oncol.* 22:237-252.

Olayloye M. A., R. M. Neve, H. A. Lane, and N. E. Hyne (2000). The ErbB signaling network: receptor heterodimerization in development and cancer. *EMBO J.* 19:3159-3167.

Sitcheran R., P. Gupta, P. B. Fisher, and A. S. Baldwin (2005). Positive and negative regulation of EAAT2 by NF-kappaB: a role for N-myc in TNFalpha-controlled repression. *EMBO. J.* 24:510-20.

Sun L. and G. Carpenter (1998). Epidermal growth factor activation of NF-kappaB is mediated through IkappaBalpha degradation and intracellular free calcium. *Oncogene* 16:2095-102.

Van Huffel S., F. Delaei, K. Heyninck, D. De Valck, and R. Beyaert (2001). Identification of a novel A20-binding inhibitor of nuclear factor-kappa B activation termed ABIN-2. *J. Biol. Chem.* 276:30216-30223.

Yarden Y. and M. X. Sliwkowski (2001). Untangling the ErbB signaling network. *Nat. Rev. Mol. Cell. Biol.* 2:127-137.

Zhivotovsky B. and S. Orrenius (2003). Defects in the apoptotic machinery of cancer cells: Role in drug resistance. *Sem. Cancer Biol.* 13:125-134.

The invention claimed is:

1. A method of treating a tumor cell overexpressing an epidermal growth factor-family receptor (ErbB), the method comprising delivering to said tumor cell a functional fragment of full-length A20-Binding Inhibitor of NF KappaB (ABIN), wherein said fragment comprises the minimal active domain (MAD).

2. The method according to claim 1, wherein said ErbB overexpressing tumor is selected from the group consisting of non-small cell lung cancer, squamous cell carcinoma of head and neck cancer, esophageal and gastric cancer, colon cancer, pancreatic cancer, breast cancer, ovarian cancer, bladder cancer, vulvar squamous carcinoma, human androgen-insensitive prostate cancer, renal carcinoma, glioma, and glioblastoma.

3. A method of treating a tumor cell overexpressing an epidermal growth factor-family receptor (ErbB), the method comprising delivering to said tumor cell a functional fragment of an A20-Binding Inhibitor of NF KappaB (ABIN) derivative, wherein said fragment comprises the Minimal Active Domain (MAD) and wherein said ErbB overexpressing tumor cell is selected from the group consisting of non-small cell lung cancer, squamous cell carcinoma of head and neck cancer, esophageal and gastric cancer, colon cancer, pancreatic cancer, breast cancer, ovarian cancer, bladder cancer, vulvar squamous carcinoma, human androgen-insensitive prostate cancer, renal carcinoma, glioma, and glioblastoma.

* * * * *

UNITED STATES PATENT AND TRADEMARK OFFICE
CERTIFICATE OF CORRECTION

PATENT NO. : 7,893,026 B2
APPLICATION NO. : 11/918559
DATED : February 22, 2011
INVENTOR(S) : Rudi Beyaert, Hilde Revets and Lieven Huang It is certified that error appears in the above-identified patent and that said Letters Patent is hereby corrected as shown below:

On the title page:

In ITEM (54) and         Change "(A20 -BINDING INHIBITOR OF
    COLUMN 1, LINES 2, 3,    NF KAPPAB)" to
    --(A20-BINDING INHIBITOR OF NF-KAPPAB)--

COLUMN 4, LINE 33,      Change "starved left" to --starved for 24 hours in ITS (insulin/transferin/selenium) containing serum-free medium. Cells were then left--

COLUMN 4, LINE 47,      Change "$\epsilon$-galactosidase" to --$\beta$-galactosidase--

Signed and Sealed this
Twenty-sixth Day of February, 2013

Teresa Stanek Rea
*Acting Director of the United States Patent and Trademark Office*